US011047859B2

(12) United States Patent
Karlsson

(10) Patent No.: US 11,047,859 B2
(45) Date of Patent: Jun. 29, 2021

(54) NORMALIZATION OF MASS TRANSPORT PROPERTIES ON OPTICAL SENSOR SURFACES

(71) Applicant: CYTIVA SWEDEN AB, Uppsala (SE)

(72) Inventor: Olof Karlsson, Uppsala (SE)

(73) Assignee: CYTIVA SWEDEN AB, Uppsala (SE)

(*) Notice: Subject to any disclaimer, the term of this patent is extended or adjusted under 35 U.S.C. 154(b) by 365 days.

(21) Appl. No.: 15/317,619

(22) PCT Filed: Jun. 19, 2015

(86) PCT No.: PCT/EP2015/063870
§ 371 (c)(1),
(2) Date: Dec. 9, 2016

(87) PCT Pub. No.: WO2015/197500
PCT Pub. Date: Dec. 30, 2015

(65) Prior Publication Data
US 2017/0122961 A1 May 4, 2017

Related U.S. Application Data

(60) Provisional application No. 62/016,208, filed on Jun. 24, 2014.

(51) Int. Cl.
*G01N 21/552* (2014.01)
*G01N 33/68* (2006.01)
*G01N 21/27* (2006.01)

(52) U.S. Cl.
CPC ........ *G01N 33/6827* (2013.01); *G01N 21/553* (2013.01); *G01N 21/274* (2013.01); *G01N 2201/127* (2013.01)

(58) Field of Classification Search
CPC ............... G01N 21/274; G01N 21/553; G01N 2201/127; G01N 33/6827; G01N 33/68; G01N 21/552; G01N 21/27
See application file for complete search history.

(56) References Cited

U.S. PATENT DOCUMENTS 4,164,558 A * 8/1979 von Schulthess ............................ G01N 33/54393
435/7.25
6,673,533 B1 * 1/2004 Wohlstadter .......... B01L 3/5027
204/400

(Continued)

FOREIGN PATENT DOCUMENTS

CN 101065665 A1 10/2007
JP H04501606 A 3/1992

(Continued)

OTHER PUBLICATIONS

Jonsson et al., "Real-Time Biospecific Interaction Analysis Using Surface Plasmon Resonance and a Sensor Chip Technology", Biotechniques, Natick, MA, US, vol. 11, No. 5, Jan. 1, 1991, pp. 620-622.

(Continued)

*Primary Examiner* — Christopher L Chin
*Assistant Examiner* — Richard Moerschell
(74) *Attorney, Agent, or Firm* — Jeff B. Vockrodt; Culhane Meadows, PLLC

(57) ABSTRACT

The invention relates to a method for normalization of a label-free system for calibration-free concentration analysis. The method comprises (1) providing a solution containing a control macromolecular particle of a known concentration at a pH lower than the pI of the macromolecular particle and a low ionic strength; (2) contacting the solution with a negatively charged optical sensor surface at a first flow rate to allow electrostatic binding of the macromolecular particle to the surface and obtaining a first sensorgram; (3) contacting the solution with the optical sensor surface at a second flow rate to allow electrostatic binding of the macromolecular particle to the surface and obtaining a second sensorgram; and (4) fitting the sensorgrams to a binding equation to determine a measured concentration of the control;

(Continued)

wherein the optical sensor surface is not immobilized with a ligand for the control and the contacting steps are performed under mass transport limitations. Also provided is a kit for performing the method, as well as a method for determining a concentration of an analyte.

16 Claims, 1 Drawing Sheet

(56) References Cited

U.S. PATENT DOCUMENTS

| | | | |
|---|---|---|---|
| 2002/0135771 A1* | 9/2002 | Witty | G01N 33/558 356/445 |
| 2006/0110594 A1* | 5/2006 | Frutos | B82Y 30/00 428/332 |
| 2008/0063634 A1* | 3/2008 | Salfeld | C07K 16/244 424/130.1 |
| 2014/0147937 A1 | 5/2014 | Karlsson et al. | |
| 2015/0233926 A1* | 8/2015 | Bregant | C07F 9/653 435/7.4 |
| 2016/0244532 A2* | 8/2016 | Heywood | C09D 163/00 |

FOREIGN PATENT DOCUMENTS

| | | | | |
|---|---|---|---|---|
| JP | H06501555 A | | 2/1994 | |
| SE | WO 2013/002718 | * | 1/2013 | ........... G01N 33/543 |
| WO | 92/06380 A1 | | 4/1992 | |
| WO | 2006058237 A2 | | 6/2006 | |
| WO | 2013/002717 A1 | | 1/2013 | |
| WO | 2013002717 A1 | | 1/2013 | |
| WO | 2014/078602 A1 | | 5/2014 | |

OTHER PUBLICATIONS

International Search Report and Written Opinion regarding International Application No. PCT/EP2015/063870, dated Aug. 25, 2015, 13 pages.
China Office Action corresponding to Chinese Application No. 201580034475.5, dated Jan. 30, 2019.
China First Search Report corresponding to Chinese Application No. 201580034475.5, dated Jan. 21, 2019.
Jönsson, U. et al., "Real-Time Biospecific Interaction Analysis Using Surface Plasmon Reasonance and a Sensor Chip Technology", BioFeature, vol. 11, No. 5 (1991).
Japan Office Action corresponding to Japanese Application No. 2016574450, dated Jun. 11, 2019.
China Office Action corresponding to Chinese Application No. 201580034475.5, dated Mar. 19, 2020.

* cited by examiner

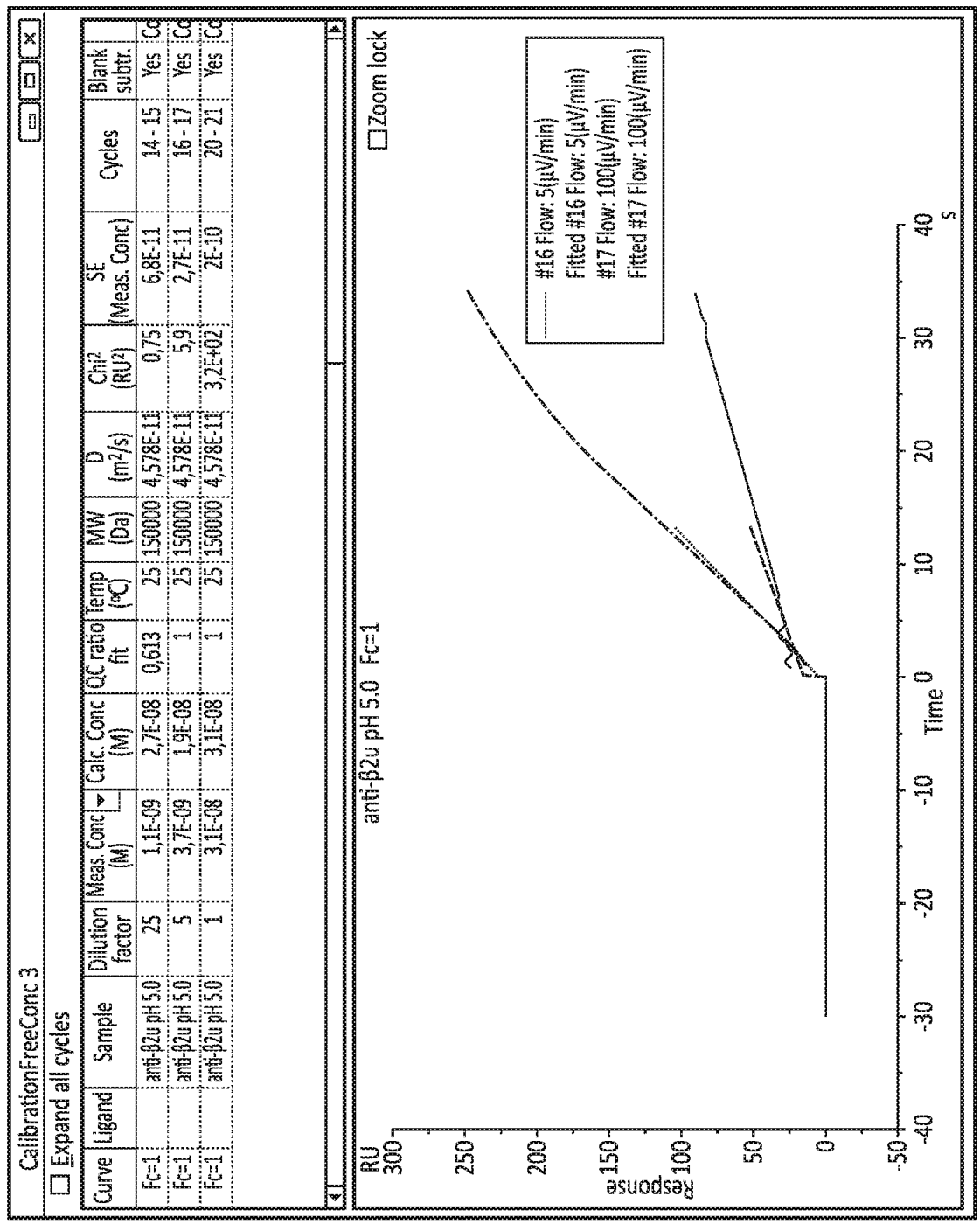

US 11,047,859 B2

NORMALIZATION OF MASS TRANSPORT PROPERTIES ON OPTICAL SENSOR SURFACES

CROSS-REFERENCE TO RELATED APPLICATIONS

This application is a filing under 35 U.S.C. 371 of international application number PCT/EP2015/063870, filed Jun. 19, 2015, which claims priority to U.S. application No. 62/016,208, filed Jun. 24, 2014, the entire disclosures of each of which are hereby incorporated by reference.

FIELD OF THE INVENTION

The present invention relates to a method for the normalization of mass transport properties on optical sensor surfaces. More specifically, the invention relates to normalization of a label-free system for calibration-free concentration analysis, and a method for determining a concentration of an analyte. The invention also relates to a kit useful for performing steps of the method.

BACKGROUND OF THE INVENTION

Analytical sensor systems (i.e., label-free systems) that can monitor molecular interactions in real time are gaining increasing interest. These systems are often based on optical biosensors and usually referred to as interaction analysis sensors or biospecific interaction analysis sensors. A representative biosensor system is the Biacore® instrumentation sold by GE Healthcare Life Sciences, which uses surface plasmon resonance (SPR) for detecting interactions between molecules in a sample and molecular structures immobilized on a sensing surface. With the Biacore® systems it is possible to determine in real time without the use of labeling not only the presence and concentration of a particular molecule in a sample, but also additional interaction parameters such as, for instance, the association rate and dissociation rate constants for the molecular interaction. The apparatus and theoretical background are fully described in the literature (see e.g., Jonsson, U., et al., BioTechniques 11: 620-627 (1991)). Normally, the technique involves the immobilization of a ligand to the special optical sensor surface of a sensor chip (flow cell), contacting the sensor chip with a flow of sample containing the analyte of interest, and then measuring the change in the surface optical characteristics of the sensor chip arising from the binding between the ligand and the analyte. For further details on SPR, reference is also made to U.S. Pat. Nos. 5,313,264, 5,573,956 and 5,641,640.

Calibration-free concentration analysis (CFCA) calculates the analyte concentration from the measured mass transport properties and values for the diffusion coefficient and molecular weight, provided as evaluation variables when the assay is run. The evaluation is based on fitting the sensorgram data to a model of interaction kinetics that contains a mass transport component. The mass transport parameters are calculated from the supplied diffusion coefficient, flow cell characteristics and molecular weight. With the analyte concentration set as a globally fitted variable the unknown concentration of the analyte can be determined. For CFCA, the flow cell characteristics might vary between individuals, this can be corrected for by using interactions between an immobilized ligand and ananalyte with known concentration. Differences in different chip individuals can theoretically cause significant variation alone. Such variation may be hard to correct for since the correction will consume the chip.

There is a need, therefore, for a general binding procedure that improves the process and reduces variation among the different chips by correction without using up the chip.

BRIEF SUMMARY OF THE INVENTION

Disclosed herein includes a novel use of electrostatic binding for normalization of mass transport properties of an optical sensing surface in flowcells. The methods use electrostatic binding of positively charged macromolecular particle to the carboxydextran surface of an optical sensing surface of, e.g., Biacore sensor chips (CM5, CM7, CM4, CM3, & C1), that occurs at pH below pI and low ionic strength, to characterize the mass transport properties of a flow cell. The electrostatically bound macromolecular particles are washed away when buffer with physiological ionic strength is flown over the chip. Such electrostatic binding may also be used here for measuring the concentration of an analytes. Furthermore, as the measurement of this method is not dependent on the active concentration of the analyte, it can also be used to measure or set the accuracy of CFCA in conjunction with spectroscopic or other non-activity dependent concentration determination methods.

Thus, a first aspect of the present invention is to provide a method for normalization of a label-free system for calibration-free concentration analysis, comprising the following ordered steps:
  (1) providing a solution containing a control macromolecular particle of a known concentration at a pH lower than the pI of the macromolecular particle protein and a low ionic strength;
  (2) contacting the solution with a negatively charged optical sensor surface at a first flow rate to allow electrostatic binding of the macromolecular particle to the surface and obtaining a first sensorgram;
  (3) contacting the solution with the optical sensor surface at a second flow rate to allow electrostatic binding of the macromolecular particle to the surface and obtaining a second sensorgram; and
  (4) fitting the sensorgrams to a binding equation to determine a measured concentration of the control macromolecular particle;
wherein the optical sensor surface is not immobilized with a ligand for the control macromolecular particle and wherein the contacting steps are performed under mass transport limitations.

In certain embodiments, the control macromolecular particle is provided in a concentration series, and the normalization is achieved by measuring electrostatic binding between the series of sample concentrations and the optical sensor surface.

In certain embodiments, the optical sensor surface is part of a detector based upon evanescent wave sensing. Preferably, the optical sensor surface is part of a detector based upon surface plasmon resonance.

In certain embodiments, the macromolecular particle is a protein.

A second aspect of the present invention is to provide a method for determining a concentration of an analyte, comprising:
  1) providing a solution containing the analyte at a pH lower than the pI of the analyte and a low ionic strength;

2) contacting the solution with a negatively charged optical sensor surface at a first flow rate to allow electrostatic binding of the analyte to the surface and obtaining a first sensorgram;

3) contacting the solution with the negatively charged optical sensor surface at a second flow rate to allow electrostatic binding of the analyte to the surface and obtaining a second sensorgram; and 4) determining the concentration of the analyte by fitting the sensorgrams to a binding equation;

wherein the optical sensor surface is not immobilized with a ligand for the control macromolecular particle and wherein the contacting steps are performed under mass transport limitations.

In certain embodiments, the analyte is a protein of interest. In certain embodiments, the protein analyte is provided in a concentration series, and the concentration measurement is achieved by measuring electrostatic binding between some of the series of diluted sample and the optical sensor surface.

In certain embodiments, the optical sensor surface is part of a detector based upon evanescent wave sensing. Preferably, the optical sensor surface is part of a detector based upon surface plasmon resonance.

A third aspect of the present invention is to provide a kit, comprising a solution of a known macromolecular particle at a known concentration; a buffer of low pH and low ionic strength for dilution of the macromolecular particle solution; and an instruction manual; wherein the kit is suitable for use in a label-free system for normalizing the optical sensor surface for calibration-free concentration analysis of an analyte.

In certain embodiments, the kit further comprising a buffer of higher ionic strength for washing off any macromolecular particle attached to the optical sensor surface.

In certain embodiments, the macromolecular particle solution in the kit has a pH lower than the pI of the macromolecular particle.

In certain embodiments, the known macromolecular particle is a protein.

Further details and advantages of the present invention will appear from the description and claims below.

BRIEF DESCRIPTION OF THE DRAWINGS

FIG. 1 shows resultant sensorgrams from electrostatic binding of anti-β2μ on the Biacore optical sensor surface, run at 5 and 100 μl/min flow rate in separate cycles.

DETAILED DESCRIPTION OF THE INVENTION

In order to assess the mass transport property in a flow cell of an analytical sensor system, one has to record initial analyte binding rates to the surface at various flow rates. The binding rate is dependent on flow rate under mass transport limited conditions. The invention takes advantage of mass transport limited binding between an analyte with known concentration and the optical sensor surface of the sensor chip to normalize the label-free detection system or measure the concentration of an analyte with unknown concentration. Such binding is achieved through electrostatic attraction of a cationic analyte to the anionic negatively charged matrix on a sensor chip. Most macromolecular particles (e.g., proteins) become cationic when the pH of the buffer is below their isoelectric point. If the ionic strength in the sample solution is low enough (~10 mM) not to shield the charges of protein and chip matrix, the protein binds to the optical sensor surface. The electrostatic binding is followed in real time under strictly mass transport limited conditions to characterize the current mass transport properties in flow cells.

In certain embodiments, electrostatic binding under strictly mass transport limited conditions is used to normalize the measured concentration accuracy, e.g., off/between different flow cells. A well characterized macromolecular particle (e.g., protein) under well characterized conditions (pH, ionic strength, concentration), is used to normalize an analytical sensor system for CFCA using proper software tools. Furthermore, as the measurement is not dependent on the active concentration of the analyte, it may be used to measure or set the accuracy of CFCA in conjunction with spectroscopic or other non-activity dependent concentration determination methods. This method is very important to make CFCA feasible and accurate for multi-channel systems because in such a system, all the channels have to be normalized to achieve high accuracy.

In one embodiment, it is provided a method for normalization of a label-free system for calibration-free concentration analysis, comprising the following ordered steps:

(1) providing a solution containing a control macromolecular particle of a known concentration at a pH lower than the pI of the macromolecular particle and a low ionic strength;

(2) contacting the solution with a negatively charged optical sensor surface at a first flow rate to allow electrostatic binding of the macromolecular particle to the surface and obtaining a first sensorgram;

(3) contacting the solution with the optical sensor surface at a second flow rate to allow electrostatic binding of the macromolecular particle to the surface and obtaining a second sensorgram; and (4) fitting the sensorgrams to a binding equation to determine a measured concentration of the control macromolecular particle;

wherein the optical sensor surface is not immobilized with a ligand for the control macromolecular particle and wherein the contacting steps are performed under mass transport limitations.

A "control macromolecular particle" may be any macromolecular particle that is positively charged, having known diffusion co-efficient as proteins, and stable during the measurement at the low pH. The macromolecular particle may be, but is not limited to, a protein, a synthetic molecule, a polysaccharide, an aptamer, or a nucleic acid molecule. Preferably, the control macromolecular particle has a molecular mass of about 5000 Dalton to about 500,000 Dalton. Preferably, the control macromolecular particle is a protein, As an example the control protein may be a monoclonal antibody.

The macromolecular particle has a known concentration. In certain embodiments, the known concentration is in the range of 0.1-20 nM. In more preferred embodiments, the known concentration is in the range of 1-20 nM. In certain embodiments, the macromolecular particle may be from a concentrated sample and is diluted prior to use. A proper concentration of the macromolecular particle ensures that the electrostatic binding reaches the proper initial binding rate and QC-ratio, and varies for different macromolecular particles.

When a macromolecular particle, e.g., a protein is in a solution having a pH lower than the pI of the protein, the protein is positively charged. pI is the pH at which the protein has a zero net charge. At a pH higher than pI, acidic groups on the protein become deprotonated leading to a net negative charge on the protein. When pH is below pI, basic groups on the protein become protonated leading to a net positive charge on the protein.

In certain embodiments, the control macromolecular particle is in a solution having a low ionic strength. By a low ionic strength, it is meant an ionic strength of between about 0-50 mM, preferably between about 5-20 mM, and more preferably about 10 mM.

In certain embodiments, the optical sensor surface is negatively charged. The optical sensor surface may, for example, be functionalized with carboxyl groups. At low ionic strength, the positively charged macromolecular particle (e.g., protein) would bind to the carboxyl group functionalized surface, since carboxyl groups are negative and the proteins are positive so they attract and there are not enough other ions around to shield the attraction. Preferably, the optical sensor surface is functionalized with carboxydextran. More preferably, the optical sensor surface is functionalized with carboxymethyl-modified dextran.

At a very low pH, the acidic ions would begin to protonate negative charges on the optical sensor surface, and lowers the capacity of the surface. Thus, a preferred pH is one that is lower than the pI of the control macromolecular particle (or analyte), while not too low to cause the sensor surface to lose capacity. In certain embodiments, a preferred pH is between pH 3-7.

In certain embodiments, the method for normalization of a label-free system for calibration-free concentration analysis further comprises calculating a correction factor for the sensor surface by comparing the measured concentration with the known concentration, for subsequent calibration-free concentration analysis of an analyte on the same optical sensor surface. In certain embodiments, the correction factor is a ratio of the known concentration to the measured concentration. Therefore, subsequently measured concentration of any analyte may be adjusted using the correction factor to arrive at the true concentration.

In certain embodiments, the method for normalization of a label-free system for calibration-free concentration analysis, further comprises, between steps 2 and 3, washing the optical sensor surface with a buffer of higher ionic strength to remove the bound macromolecular particle from the surface. In certain other embodiments, the method further comprises, after step 3, washing the optical sensor surface with a buffer of higher ionic strength to remove the bound macromolecular particle from the surface. The buffer of higher ionic strength has an ionic strength higher than that of the control macromolecular particle solution. Thus, in certain embodiments, the higher ionic strength may be about 50-500 mM. Preferably, the ionic strength of the buffer may be about 100-200 mM, such as 150-180 mM.

In certain embodiments, the first and second flow rates are different. In certain embodiments, the first flow rate may be about 5-20 ul/min, and the second flow rate may be about 50-100 ul/min. In other embodiments, the first flow rate may be about 50-100 ul/min, and the second flow rate may be about 5-20 ul/min. Preferably, first flow rate may be about 5 ul/min and the second flow rates may be about 100 ul/min.

In certain embodiments, electrostatic binding under strictly mass transport limited conditions is used to measure the concentration of an analyte of interest. Such concentration, under well characterized conditions (pH, ionic strength, concentration dilution), may be obtained using an analytical sensor system by calibration-free concentration analysis with proper software tools. Unlike the concentration measurement obtained in the presence of a ligand on the optical sensor surface, the measurement does not require the binding between the analyte and a ligand. Therefore, the measurement does not distinguish between analytes that are "active" (i.e., capable of binding to a ligand) and those that are inactive. It is the total concentration that is measured as compared to the "active" concentration.

Thus, in one embodiment, it is provided a method for determining a concentration of an analyte, comprising:
(1) providing a solution containing said analyte at a pH lower than the pI of the analyte and a low ionic strength;
(2) contacting the solution with a negatively charged optical sensor surface at a first flow rate to allow electrostatic binding of the analyte to the surface and obtaining a first sensorgram;
(3) contacting the solution with the negatively charged optical sensor surface at a second flow rate to allow electrostatic binding of the analyte to the surface and obtaining a second sensorgram; and
(4) determining the concentration of the analyte by fitting the sensorgrams to a binding equation;
wherein the optical sensor surface is not immobilized with a ligand for the control macromolecular particle and wherein the contacting steps are performed under mass transport limitations.

In certain embodiments, the method further comprises, between steps 2 and 3, a step of washing the optical sensor surface with a buffer of higher ionic strength to remove the bound analyte from the surface.

In certain embodiments, the method further comprises an optional step, after step 3, of washing the optical sensor surface with a buffer of higher ionic strength to remove the bound analyte from the surface.

In certain embodiments, the first and second flow rates are different. In certain embodiments, the first flow rate may be about 5-20 ul/min, and the second flow rate may be about 50-100 ul/min. In other embodiments, the first flow rate may be about 50-100 ul/min, and the second flow rate may be about 5-20 ul/min. Preferably, first flow rate may be about 5 ul/min and the second flow rates may be about 100 ul/min.

In certain embodiments, the method further comprising measuring the concentration of the analyte with an alternative measurement and comparing the measured concentrations. In certain embodiments, the alternative measurements for analyte concentrations are traditional methods, such as absorbance at 280 nm using a spectrophotometer for proteins.

In certain embodiments, an analyte may be any macromolecular particle, such as a chemical compound or a biological molecule which is positively charged in the solution. The macromolecular particle may, for example, be a protein, a polysaccharide, a nucleic acid molecule. In certain preferred embodiments, the analyte is a protein such as an antibody, or a virus particle.

The macromolecular particle solution is serially diluted prior to use. A proper concentration of the macromolecular particle ensures that the electrostatic binding reaches the proper initial binding rate and QC-ratio, and varies for different macromolecular particles. A proper dilution may be determined by fitting the sensorgrams to the 1:1 interaction kinetics model (see below).

In certain embodiments, electrostatic binding under strictly mass transport limited conditions is used to assess the activity of a protein preparation. After a total concentration is measured as described above, the active concentration of an analyte is measured with CFCA, in the presence of immobilized ligand (e.g., in a parallel flow cell). By this combination the degree of activity in a preparation can be determined.

The following general principles are applicable for all aspects of the invention.

Surface binding interactions may be characterized using a number of different interaction analysis techniques. Commercially available biosensors include the above-mentioned Biacore® system instruments, which are based on surface plasmon resonance (SPR) and permit monitoring of surface interactions in real time.

The phenomenon of SPR is well known. SPR arises when light is reflected under certain conditions at the interface between two media of different refractive indices, and the interface is coated by a metal film, typically silver or gold. In the Biacore® instruments, the media are the sample and the glass of a sensor chip that is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the Biacore® system the sample side.

When molecules in the sample bind to the sensor chip surface, the concentration, and therefore the refractive index at the surface changes and an SPR response is detected. Plotting the response against time during the course of an interaction will provide a quantitative measure of the progress of the interaction. Such a plot is usually called a sensorgram. In the Biacore® system, the SPR response values are expressed in resonance units (RU). One RU represents a change of 0.00001° in the angle of minimum reflected light intensity, which for most proteins is roughly equivalent to a change in concentration of about 1 pg/mm² on the sensor surface. As sample containing an analyte contacts the sensor surface, the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicated on the sensorgram by a drop in RU over time as analyte dissociates from the surface-bound ligand.

Calibration-free concentration analysis calculates the analyte concentration from the measured mass transport properties and values for the diffusion coefficient and molecular weight, provided as evaluation variables when the assay is run. In one example, the evaluation is based on fitting the sensorgram data to a model of 1:1 interaction kinetics, with mass transport parameters calculated from the supplied diffusion coefficient, flow cell characteristics and molecular weight, and with the analyte concentration set as a globally fitted variable.

The events in the flow cell and on the sensor surface can be described as follows:

The binding of a macromolecular particle, e.g., a protein in the bulk ($A_{bulk}$) to the chip surface (B) is a two-step process. In the first step protein from the bulk is transported to the surface ($A_{surf}$) with mass transport coefficient $k_m$, and in the second step, the binding between $A_{surf}$ and B occurs with association constant $k_a$ and dissociation constant $k_d$ and complex AB is formed.

If the transport of $A_{bulk}$ to sensor surface is slower than binding of $A_{surf}$ to B, then the mass transport limitation occurs and analyte concentration can be measured.

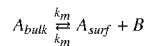

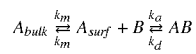

The experimental procedure includes monitoring of responses on at least two widely separated flow rates and evaluation with appropriate model.

The binding phases of the curves (i.e., sensorgrams) obtained from such an experiment are fitted to a bi-molecular interaction model with mass transfer term ($k_t$), in which analyte concentration (Conc) is a fitted parameter:

A(solution)=Conc
A[0]=0
dA/dt=kt*(Conc-A)-(ka*A*B-kd*AB)
B[0]=RMax
dB/dt=-(ka*A*B-kd*AB)
AB[0]=0
dAB/dt=(ka*A*B-kd*AB)
Total response:
AB+RI In this model, the value of the mass transport constant, kt, is introduced as a constant, which is calculated according to a formula:

$$k_t = G \times Mw \times 0.98 \times \sqrt[3]{\frac{D^2 \times f}{0.3 \times h^2 \times w \times l}}$$

where G is factor G, $Mw$ is Molecular weight, $D^2$ involves diffusion coefficient, $f$ is flow rate, and $h$, $w$, $l$ are height, width, length of the flow cell.

If we group the parameters in this formula into protein-dependent and instrument-dependent, we obtain:

$$k_t = \underbrace{Mw \times \sqrt[3]{D^2} \times G \times 0.98}_{\text{analyte-dependent parameters Const}_{analyte}} \times \underbrace{\sqrt[3]{\frac{1}{(0.3 \times h^2 \times w \times l)}}}_{\text{instrument-dependent parameters Const}_{instr}} \times \underbrace{\sqrt[3]{f}}_{\text{variable}}$$

Or:

$$k_t = G \times Const_{analyte} \times Const_{instr} \times \sqrt[3]{f}$$

Runs for calibration-free concentration analysis require a minimum of two cycles for each sample, run at different flow rates. Blank cycles for each flow rate are optional.

It is important that the sensorgrams at the lowest and highest flow rates (e.g., 5 and 100 μl/min respectively) are sufficiently separated. If the curves are close together or coincide, this indicates that there is not sufficient mass transport limitation in the binding for reliable concentration measurement. Sufficient mass transport limitation is generally indicated by a value for the QC ratio of about 0.2 or higher. Samples with low QC ratios should be treated with caution.

The QC ratio is calculated as follows from the quotient Q which reflects the degree of mass transport limitation (initial binding is measured by the slope of sensorgram in RU per second):

quotient $Q$=(initial binding at high flow rate/initial binding at low flow rate)*(low flow rate/high flow rate)$^{1/3}$ Under conditions of complete mass transport limitation, the binding rate is proportional to the cube root of the flow rate, so the quotient Q has a value of 1. When there is no mass transport limitation, the binding rate is independent of the flow rate so Q has a value equal to the cube root of the flow rate ratio. The range of possible theoretical values for Q will thus depend on the flow rates used (for flow rates of 5 and 100 µl/min, the value is 0.37). The QC ratio is calculated from the measured value for Q normalized to a scale of 0-1:

$Q_{max}$=1

$Q_{min}$=(low flow rate/high flow rate)$^{1/3}$

QC ratio=($Q$ measured-$Q_{min}$)/($Q_{max}$-$Q_{min}$)

Occasionally, the measured binding rate may be lower at the higher flow rate, leading to a negative value for the QC ratio. This can occur if the sensorgrams are disturbed or as a result of experimental variation when the binding rate is not affected by flow rate (so the binding rates should in theory be equal and the QC ratio should be 0).

Measured concentration is the value calculated from the fitting, and actual concentration is obtained by multiplying the measured concentration and the dilution factor to give the concentration in the original sample. In certain embodiments, a correction factor obtained according to embodiments of the invention is applied in calculating the actual concentration of an analyte.

While the description above has been made with some respect to the Biacore® systems, it is understood that the invention may be used in connection with numerous other techniques for detecting binding interactions at the solid support surface, including, e.g., those relying on a label, such as a radiolabel, a chromophore, a fluorophore, a marker for scattering light, an electrochemically active marker (e.g., field effect transistor based potentiometry), an electric field active marker (electro-stimulated emission), a magnetically active marker, a thermoactive marker, a chemiluminescent moiety or a transition metal, as well as so-called label free detection systems. Real time detection systems are, however, preferred, especially those based on chemical sensor or biosensor technology.

A biosensor is broadly defined as a device that uses a component for molecular recognition (for example a layer with immobilized antibodies) in either direct conjunction with a solid state physicochemical transducer, or with a mobile carrier bead/particle being in conjunction with the transducer. While such sensors are typically based on label free techniques, detecting, e.g., a change in mass, refractive index, or thickness for the immobilized layer, there are also sensors relying on some kind of labelling. Typical sensor detection techniques include, but are not limited to, mass detection methods, such as optical, thermo-optical and piezoelectric or acoustic wave (including, e.g., surface acoustic wave (SAW) and quartz crystal microbalance (QCM)) methods, and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) which may include scatter enhancing labels, optical wave guide sensors; external reflection imaging, evanescent wave-based imaging such as critical angle resolved imaging, Brewster angle resolved imaging, SPR angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaky mode spectroscopy, reflective interference spectroscopy (RIfS), transmission interferometry, holographic spectroscopy, and atomic force microscopy (AFR).

Commercially available today are inter alia bio sensor systems based on SPR. Exemplary such SPR-biosensors include the above-mentioned Biacore® instruments. A detailed discussion of the technical aspects of the Biacore® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the Biacore® instruments may be found in U.S. Pat. No. 5,492,840. The full disclosures of the above-mentioned U.S. patents are incorporated by reference herein.

It may many times be convenient to carry out the method of the invention in a flow cell, e.g., of the type used in the above-mentioned Biacore® instruments. Other flow cells that may be used in the present invention are also well known to the skilled person and need not be described herein.

It is to be noted that the term "solid support" as used herein is to be interpreted broadly and is meant to comprise any solid (flexible or rigid) substrate onto which molecular interactions therewith can be detected by the particular detection system chosen. The substrate may be biological, non-biological, organic, inorganic or a combination thereof, and may be in the form of particles, strands, precipitates, gels, sheets, tubings, spheres, containers, capillaries, pads, slices, films, plates, slides, etc, having any convenient shape, including disc, sphere, circle, etc. The substrate surface may have any two-dimensional configuration and may include, for example steps, ridges, kinks, terraces and the like and may be the surface of a layer of material different from that of the rest of the substrate.

Example

CFCA was used for concentration determination of Anti-β2µ antibody through to the following steps:
1. Anti-β2µ was diluted from 1 g/l stock solution to 10 mg/l in 10 mM acetate pH 5.0, this is calculated to correspond to 67 nM (dilution factor 1)
2. The solution was further diluted 5 and 25 times with the acetate buffer.
3. All dilutions were run according to the CFCA standard Biacore method for Biacore T200 (see Biacore T200 software manual), at 5 and 100 μl/min flow rate in separate cycles monitoring the binding to a ligand free Sensor Chip CM5. Cycles with only acetate buffer were run as reference and were subtracted from the corresponding anti-β2μ cycles.

4. D factor 4,578E-11 (typical for antibodies) and molecular weight 150000 Da were entered, the QC-ratio were checked.
5. Fittings to overlay sensorgrams from the two flowrates of each dilution were performed. The preinjection baseline and the first 15 s after injection were used.
6. The software algorithm presents the determined concentration with the entered dilution factor taken into account.

The initial binding (slope of sensorgram in RU per second the first 15 s after injection start) was sufficient at the low flow rate for all three dilutions and so was the difference in initial binding rate between the two flow rates as judged from the QC-ratio. The average concentration was determined to be 26 nM.

In summary the result shows that the method gives data quality that is suitable for CFCA evaluation (FIG. 1). The vertical axis (y-axis) indicates the response (here in resonance units, RU) and the horizontal axis (x-axis) indicates the time (here in seconds, s). The diagram shows the data from dilution factor 5.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A method of mass transport properties normalization in a label-free system for calibration-free concentration analysis, comprising:
   (1) providing a solution containing a control macromolecular particle of a known concentration at a pH lower than the pI of the macromolecular particle;
   (2) contacting the solution with a negatively charged optical sensor surface at a first flow rate to allow electrostatic binding of the macromolecular particle to the surface and obtaining a first sensorgram;
   (3) contacting the solution with the optical sensor surface at a second flow rate to allow electrostatic binding of the macromolecular particle to the surface and obtaining a second sensorgram, the second flow rate being different than the first flow rate; and
   (4) determining the concentration of the analyte by fitting the first and second sensorgrams to a binding equation to determine a measured concentration of the control macromolecular particle and normalize the mass transport properties;
   wherein the contacting steps are performed under mass transport limited binding conditions, the binding of the control macromolecule at the first and second flow rates is electrostatic binding, reference samples using a only buffer were measured on the sensor surface and subtracted from the first and second sensorgrams, and the control macromolecule is not bound by a ligand at the sensor surface.

2. The method of claim 1, further comprising calculating a correction factor for the sensor surface by comparing the measured concentration with the known concentration, for subsequent calibration-free concentration analysis of an analyte on the same optical sensor surface.

3. The method of claim 1, wherein the negatively charged optical sensor surface is functionalized with carboxyl groups.

4. The method of claim 1, wherein the negatively charged optical sensor surface is functionalized with carboxydextran.

5. The method of claim 1, further comprising, between steps 2 and 3, a step of washing the optical sensor surface with a buffer of an ionic strength higher than the ionic strength of the solution to remove the bound macromolecular particle from the surface.

6. The method of claim 1, further comprising an optional step, after step 3, of washing the optical sensor surface with a buffer of an ionic strength higher than the ionic strength of the solution to remove the bound macromolecular particle from the surface.

7. The method of claim 1, wherein the first flow rate is about 5 ul/min and the second flow rates is about 100 ul/min.

8. The method of claim 1, wherein the control macromolecular particle is a control protein.

9. The method of claim 1, wherein the control macromolecular particle is a control antibody.

10. A method for determining a concentration of an analyte, comprising:
   (1) providing a solution containing said analyte at a pH lower than the pI of the analyte;
   (2) contacting the solution with a negatively charged optical sensor surface at a first flow rate to allow binding of the analyte to the surface and obtaining a first sensorgram;
   (3) contacting the solution with the negatively charged optical sensor surface at a second flow rate to allow binding of the analyte to the surface and obtaining a second sensorgram; and
   (4) determining the concentration of the analyte by fitting the first and second sensorgrams to a binding equation to determine a measured concentration of the control macromolecular particle and normalize the mass transport properties;
   wherein the contacting steps are performed under mass transport limited binding conditions, the binding of the control macromolecule at the first and second flow rates is electrostatic binding, reference samples using only a buffer were measured on the sensor surface and subtracted from the first and second sensorgrams, and the control macromolecule is not bound by a ligand at the sensor surface.

11. The method of claim 10, further comprising, between steps 2 and 3, a step of washing the optical sensor surface with a buffer of higher ionic strength than the ionic strength of the solution to remove the bound analyte from the surface.

12. The method of claim 10, further comprising an optional step, after step 3, of washing the optical sensor surface with a buffer of higher ionic strength than the ionic strength of the solution to remove the bound analyte from the surface.

13. The method of claim 10, wherein the first and second flow rates are different.

14. The method of claim 10, wherein the first flow rate is about 5 ul/min and the second flow rates is about 100 ul/min.

15. The method of claim 10, further comprising measuring the concentration of the analyte with an alternative measurement and comparing the measured concentrations.

16. The method of claim 10, wherein the analyte is a protein.

\* \* \* \* \*